United States Patent [19]

O'Day et al.

[11] Patent Number: 6,070,574

[45] Date of Patent: Jun. 6, 2000

[54] RESUSCITATOR DEVICE WITH SELF CLOSING VALVE

[75] Inventors: Therese J. O'Day, Racine, Wis.; Melvin I. Eisenberg, Gurnee, Ill.

[73] Assignee: Plasco, Inc., Gurnee, Ill.

[21] Appl. No.: 08/992,238

[22] Filed: Dec. 17, 1997

[51] Int. Cl.[7] .................................................. A62B 18/02
[52] U.S. Cl. .............................. 128/203.11; 128/202.28; 128/207.12; 128/207.16; 128/205.24
[58] Field of Search ......................... 128/203.11, 207.12, 128/202.28, 202.29, 205.24, 207.16; 137/512.15, 854

[56] References Cited

U.S. PATENT DOCUMENTS

| | | | |
|---|---|---|---|
| 1,867,478 | 7/1932 | Stelzner | 128/207.12 |
| 3,312,237 | 4/1967 | Mon et al. | 137/512.15 |
| 3,990,439 | 11/1976 | Klinger | 128/207.12 |
| 4,819,627 | 4/1989 | Connors | 128/203.11 |
| 5,127,397 | 7/1992 | Kohnke | 128/203.11 |
| 5,231,982 | 8/1993 | Harrison et al. | 128/207.12 |
| 5,398,673 | 3/1995 | Lambert | 128/203.11 |
| 5,518,026 | 5/1996 | Benjey | 137/512.15 |
| 5,704,347 | 1/1998 | Schlobohm | 128/203.11 |

FOREIGN PATENT DOCUMENTS 2204498  11/1988   United Kingdom .............. 128/203.11

*Primary Examiner*—John G. Weiss
*Assistant Examiner*—V. Srivastava
*Attorney, Agent, or Firm*—Jerome Goldberg

[57] ABSTRACT

A mouth-to-mouth resuscitator device for providing a physical barrier between a rescuer and a victim including a hollow tubular housing having an air input end and an air output end and counting a self closing one way valve having a disc shape secured between the housing ends and a pair of spaced apart rods secured to the disc for attaching the disc to a support plate, so that the inner end of the plate is received between the rods to support the valve disc and provide a hinge for dividing the disc into a pair of flaps to bend outward to an open position in response to forced air for transferring the air from the air input end to the air output end, and the flaps resiliently return to a closed position when the forced air has dissipated.

6 Claims, 4 Drawing Sheets

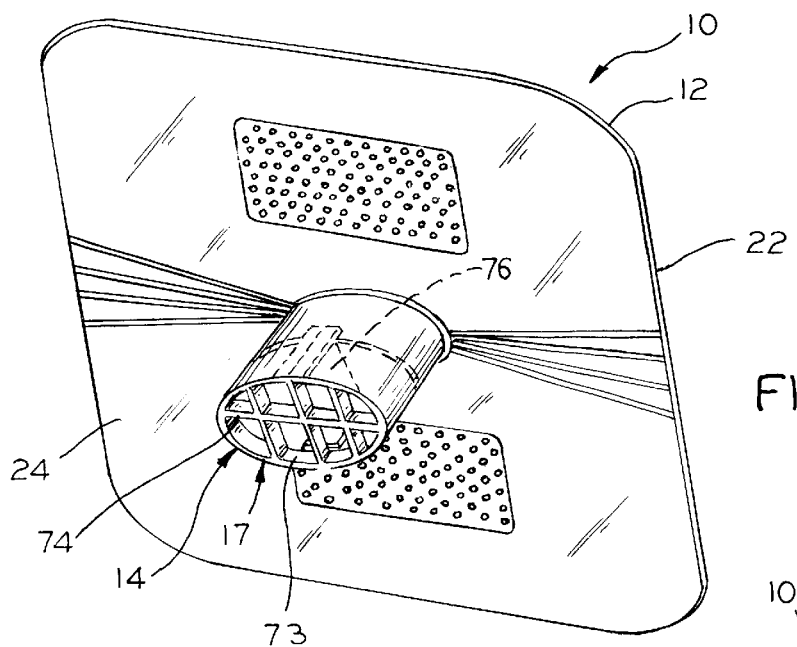
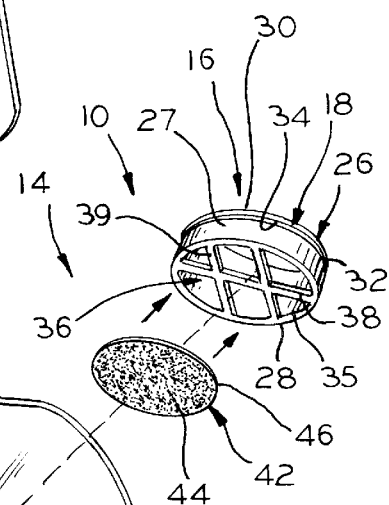
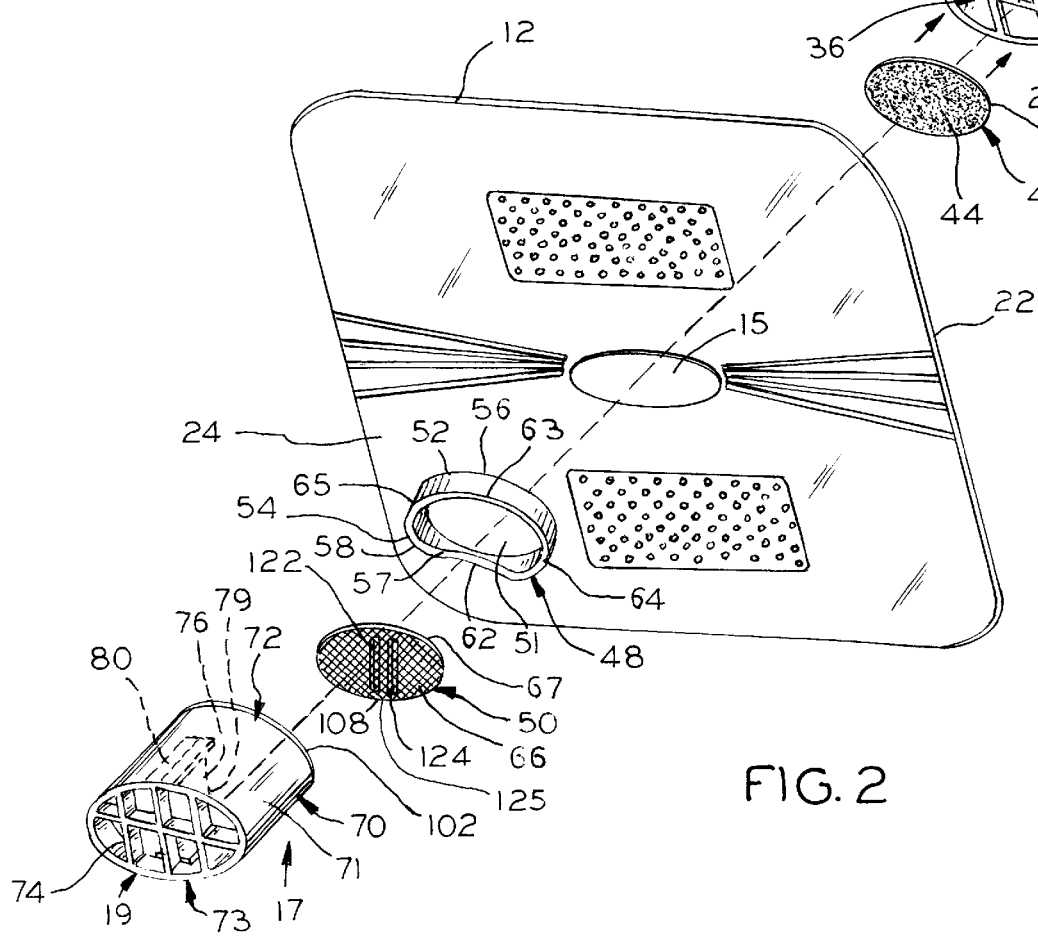
FIG. 1
FIG. 2

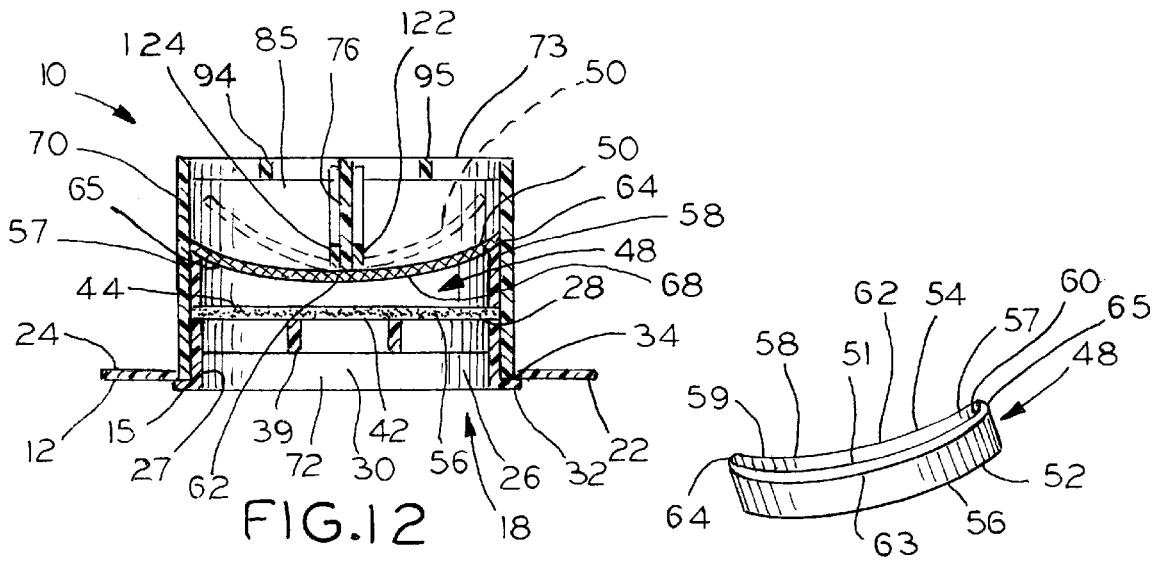
FIG.12
FIG.13
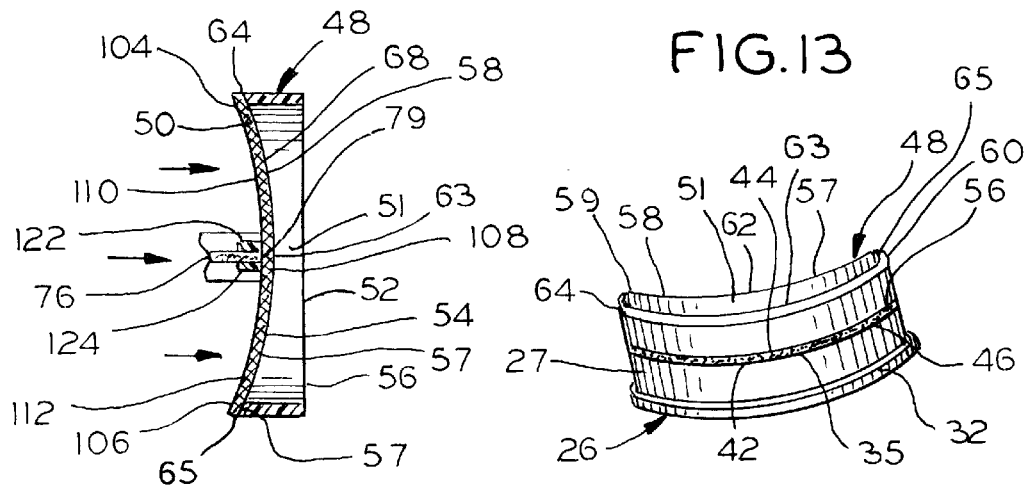
FIG.15
FIG.14
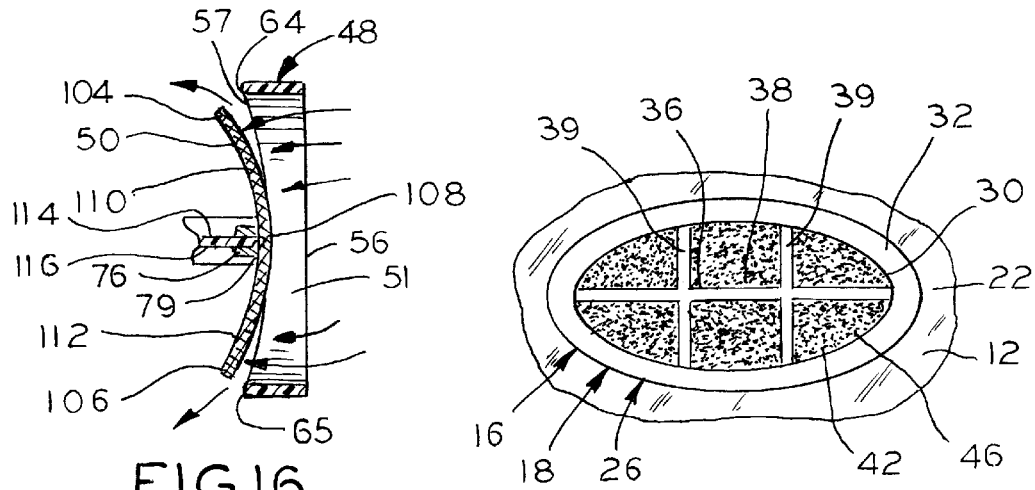
FIG.16
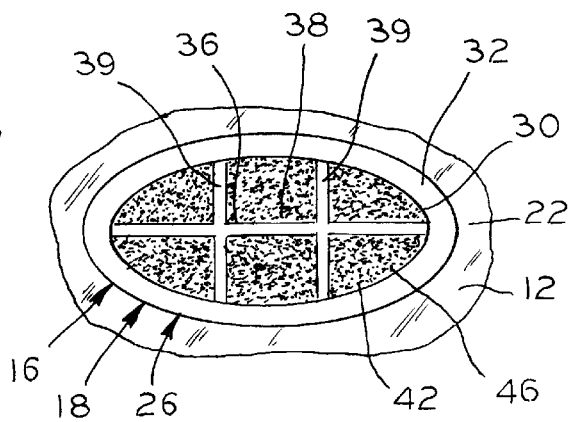
FIG.17

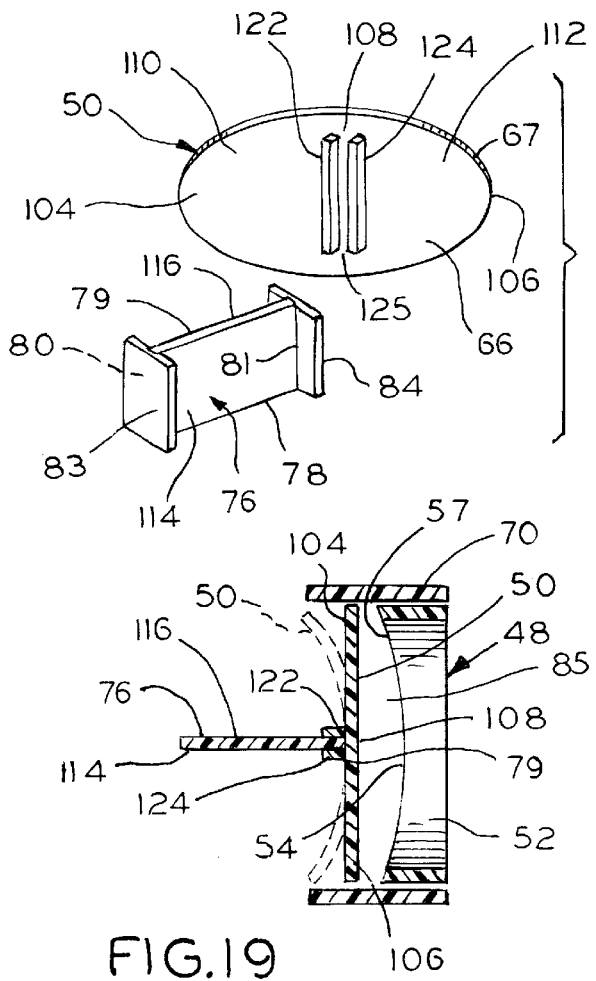
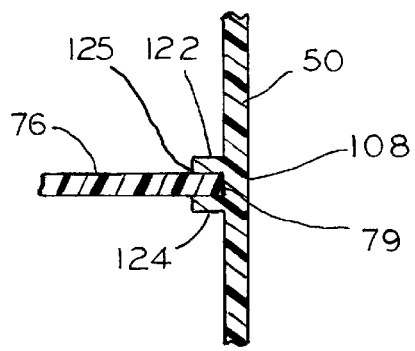
FIG. 21
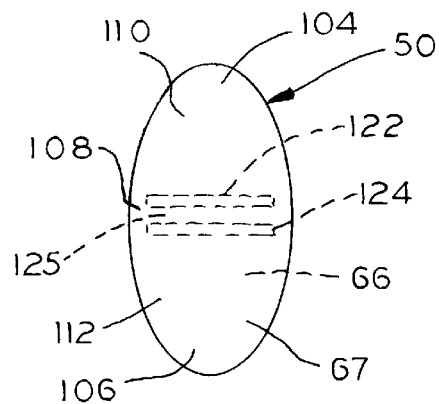
FIG. 20
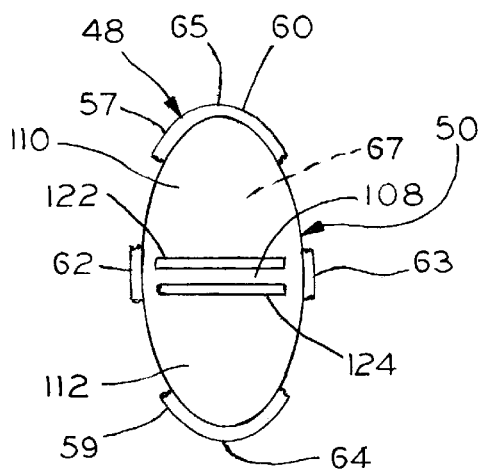
FIG. 22

RESUSCITATOR DEVICE WITH SELF CLOSING VALVE

BACKGROUND OF THE INVENTION

This invention relates generally to devices for providing mouth-to-mouth resuscitation; and more specifically relates to devices having a physical barrier between the mouth of a rescuer and the mouth of the victim. Still more particularly, the invention relates to devices having a one way, self closing valve for transferring air under pressure from a rescuer to a victim, and blocking any reverse flow of fluid from the victim to the rescuer.

Mouth-to-mouth resuscitation Is a first aid technique and a preferred method for reviving a non-breathing victim when life or death may be determined from actions taken within a period of seconds, to rapidly deliver large volumes of exhaled air under pressure to inflate the lungs and reactivate the normal breathing process. The technique most commonly used in this regard is referred to as cardiac, pulmonary resuscitation ("C.P.R.").

Resuscitator devices to provide a physical barrier between the rescuer and victim requiring mouth-to-mouth resuscitation, are widely used today and accepted. Moreover, these resuscitator devices are frequently included in first aid kits, or stored at locations where emergency medical supplies are accessed, Often these resuscitator devices are carried on the person of parties trained in C.P.R. and would be called upon to provide C.P.R. or the like during emergency situations, such as ER doctors, paramedics, etc.

U.S. Pat. No. 4,819,628 (1989), Eisenberg et al, entitled "Mouth-to-Mouth Resuscitator Device," discloses a resuscitator device having a physical barrier between the mouth of the rescuer and the mouth of the victim. The device comprises a flexible sheet having a mouth opening formed in the sheet; and a protective tube bonded around the periphery of the mouth opening and extending downward therefrom.

A self closing one way valve is positioned in the tube and included a flexible sleeve having an open air inlet adjacent the mouth opening and an air outlet adjacent the output end of the tube; and a spring strip attached to the sleeve near the air outlet for securely closing the air outlet. The rescuer exhales air under pressure into the air inlet and the forced air entering the valve spreads the sleeve walls apart and overcomes the force of the spring strip for opening the valve and discharging the exhaled deep breath into the mouth of the victim. The tube containing the valve protects the valve and directs the forced air into the lungs of the victim.

There are many instances when it is more desirable that the protective tube of the resuscitator device have a smaller length than the length of such tube presently in use. If a victim were a child or a person having a more diminutive mouth structure, a smaller protective tube would be more suitable for use and less likely to injure or damage the inside mouth structure of the victim.

In order to utilize a protective tube having a smaller length, the one way valve for the resuscitator device would be required to operate within a more confined area. The subject invention provides a mouth-to-mouth resuscitator device utilizing a valve arrangement capable of effectively operating within a smaller protective tube configuration than the longer length rigid tubes prevalent in use at the present time.

Therefore, it is a primary object of this invention to provide a mouth-to-mouth resuscitator device including a self-closing one way valve effectively operable within a protective tube having a length substantially smaller than the length of the valve protective tube generally used for mouth-to-mouth resuscitator devices.

Another object is to provide a resuscitator device for transferring exhaled air under pressure from a rescuer to a victim and blocking back flow of fluids from the victim to the rescuer.

Another object is to provide a mouth-to-mouth resuscitator device having component parts that are easily assembled together.

Another object is to prevent Impurities from being transferred from the rescuer to the patient.

SUMMARY OF THE INVENTION

The resuscitator device of this invention provides a physical shield between a rescuer and a victim or patient requiring mouth-to-mouth resuscitation. The device comprises a housing having a rescuer input end in which the rescuer exhales a deep breath under pressure and a victim output end for discharging the forced air into the mouth and lungs of the victim. A self closing, one way valve is secured in the housing and is normally in a closed-condition. The valve revolves or bends outward toward the victim to open the valve in response to said forced air, and thereby transferring the forced air from the input end to the output end. The valve resiliently revolves inward toward the rescuer air input end to return to the closed-condition, when said forced air has dissipated or is removed. The valve when in the closed-condition prevents reverse flow of fluids from the victim to the rescuer.

The valve comprises a flexible oval shaped disc having opposite free ends. The disc is secured in the housing to divide into a pair of flaps; one flap extending from one free end to the longitudinal center of the disc and the other flap extending from the other free end to the longitudinal center of the disc.

The flaps of the disc are bendable from a closed position along a lateral line passing through the longitudinal center of the disc, to open the valve and transfer the forced air to the victim output end. When the flaps of the valve are in the closed positions, the valve is closed to block passage of fluids through the device in the reverse direction from the victim air output end toward the rescuer air input end.

Hence, the flaps function as a pair of lever arms, which revolve outward in opposite directions away from the input end to open the valve in response to the forced air pressure generated by the rescuer. The flaps resiliently bend or revolve inward in opposite directions to their closed positions when the forced air has dissipated.

A plate is mounted in the housing so that an edge thereof supports the disc along a lateral line perpendicular to the longitudinal center line of the disc, to cause the bending of the disc into the pair of flaps. The plate includes a pair of opposed sides, whereby one said flap bends outwardly in one direction toward one side of the plate and the other flap bends outwardly in the opposite direction toward the other side of the plate. Therefore, the plate in cooperation with the valve disc functions as a fulcrum or hinge, to divide the disc into the pair of flaps that fold or bend outward on opposite sides of the plate, to open the valve and transfer the forced exhaled air from the rescuer to the victim air output end. When the disc (or flaps) is closed it blocks the fluid passageway through the device in the reverse direction, which may occur if the victim exhales thereby protecting the rescuer from contact with the victim's fluids.

The resuscitator device further includes a valve seat encircling a hole and has a concave shape. The valve disc has a convex shape complementary to the concave shape of the seat and rests on the seat to close the hole, when the device is in the closed-condition. The valve seat contacts the periphery of the valve disc and blocks movement of the disc from the closed-condition to an open-condition when fluids back flow from the output end to the input end.

The valve disc Is positioned in the air flow passageway, whereby reverse fluid flow forces the periphery of the disc against the valve seat to maintain the valve closed. Hence, the valve seat and the valve disc cooperate for more securely closing the valve disc in response to the back flow of fluid from the output end toward the input end.

The valve disc normally has a flat configuration (prior to being assembled in the device). Thus, the valve disc is stressed when shaped into a configuration other than flat. Hence, the valve disc is stressed in the convex shape to firmly contact the valve seat, when the valve is in the closed-condition. This is due to the concave valve seat blocking the valve disc from achieving a flat shape.

A pair of spaced apart guide rods are formed on the outer side of the valve disc and extend laterally across the disc at the substantial center thereof. The inner edge of the plate is received in the space between the guide rods to easily and properly position the valve disc inside the resuscitator device when assembling the various parts of the device.

BRIEF DESCRIPTION OF THE DRAWINGS

Referring to the drawings in which the same characters of reference are employed to indicate corresponding similar parts throughout the several figures of the drawings.

FIG. 1 is a perspective bottom view of the resuscitator device, embodying the principles of the invention;

FIG. 2 is a perspective exploded view of the resuscitator device prior to being assembled;

FIG. 12 is a central, longitudinal, sectional view of the assembled parts inside the valve housing, and showing the valve disc stressed so that the convex surface of the valve disc abuts the concave surface of the valve seat;

FIG. 13 is a perspective view of the valve seat to illustrate the concave outer edge surface of the seat;

FIG. 14 is a perspective view of the top side of the valve support secured to the filter support cap;

FIG. 15 is a schematic view of the convex valve disc in the closed-position abutting the concave edge of the valve seat;

FIG. 16 is a schematic view of the valve disc, and showing the free ends of the disc moving in opposite directions to an open-condition, for transmitting forced air from the rescuer end to the patient end of the resuscitator device;

FIG. 17 is a top view of the device(air input end of the device) and showing the filter attached to the screen of the support cap;

FIG. 18 is a perspective view of the valve disc spaced from the disc support plate and showing the guide rods on the outer side of the valve disc;

FIG. 19 illustrates the valve disc positioned on the valve support plate prior to the assembly of the valve support in the device to cause convex curvature of the valve disc;

FIG. 20 is a top view of the inner side of the valve disc and showing the guide rods in phantom;

FIG. 21 is a fragmentary sectional view to show the inner edge of the valve support plate received between the guide rods of the valve disc; and FIG. 22 is a fragmentary top or inner view showing the surfaces defining the opposed depressions of the valve seat bearing or clamping against the inner side of the valve disc at the center thereof (actually the valve seat is opposed to the inner side of the valve disc).

DESCRIPTION OF PREFERRED EMBODIMENT

Figures 3, 4, 6, 7:
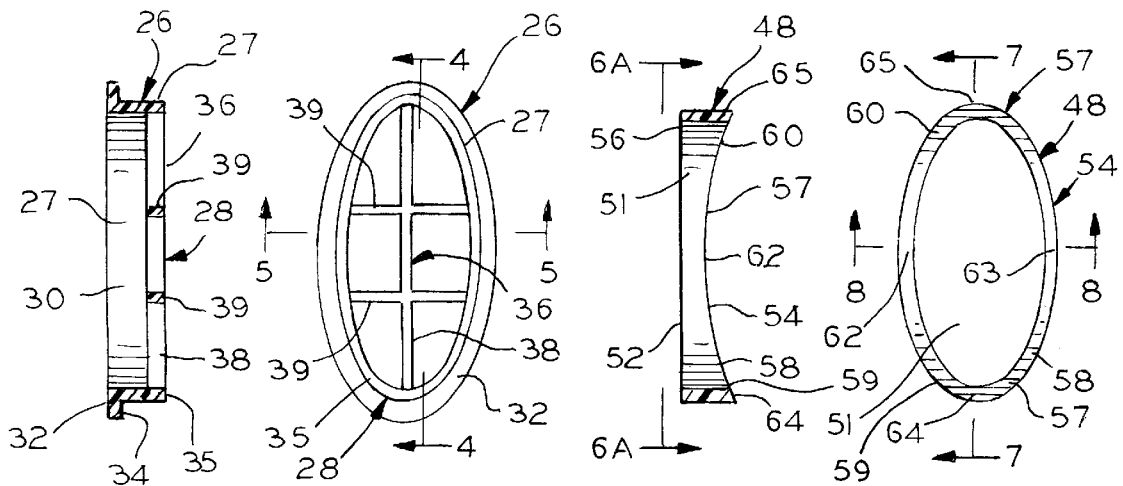
FIG. 3 is a bottom view of the filter support cap.
FIG. 4 is a longitudinal sectional view of the filter support cap, taken on the plane of the line 4—4 in FIG. 3, and viewed in the direction indicated.
FIG. 6 is a bottom view of the valve support to illustrate the valve seat.
FIG. 7 is a longitudinal sectional view of the valve seat, taken on the plane of the line 7—7 in FIG. 6, and viewed in the direction indicated.
Figure 5:
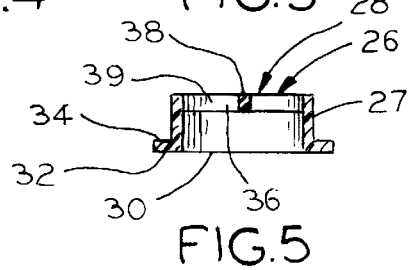
FIG. 5 is a lateral sectional view of the filter support cap, taken on the plane of the line 5—5 in FIG. 3, and viewed in the direction indicated.

Referring now more particularly to FIGS. 1 and 2 of the drawings, the reference numeral 10 indicates generally a resuscitator device for use as a physical barrier between a rescuer and a victim or patient when the rescuer is resuscitating a victim or patient. The device 10 is particularly suitable when engaging in Cardiac Pulmonary Resuscitation ("C.P.R.") or in other situations when the victim is unable or has extreme difficulty in breathing.

The resuscitator device 10 includes a flexible face shield 12 and a tubular assembly indicated generally by the reference numeral 14 which extends centrally through an opening 15 in the shield 12 and is sealed adjacent and around the opening 15. The tubular assembly 14 includes a rescuer section 16 and a valve section 17 secured together.

Air exhaled by the rescuer under pressure is applied at the inner or rescuer end 18 of the rescuer section 16 (FIG. 17). The forced air is transmitted through the tubular assembly 14; and finally discharged into the mouth of the victim via the outer or patient end 19 of the valve section 17 of the device 10.

The face shield 12 is shown having a substantially square shape, although various other shapes or configurations may be used. The opening 15 is shown having an elliptical shape and is centrally formed through the shield 12. The shield 12 includes a rescuer side 22 and a victim or patient side 24.

The rescuer section 16 includes an oval shaped, hollow support cap 26 (FIGS. 2 thru 5) having an oval shaped sidewall 27 extending between an open outer or bottom end 28 and an open inner or top end 30, as viewed in FIG. 2.

The descriptive terms, such as inner or outer or top or bottom, shall be generally considered as viewed in FIGS. 1 and 2, unless otherwise stated.

An annular flange or brim 32 (FIGS. 4, 5 and 17) circumscribes the inner end 30 of the cap 26. The side wall 27 of the cap 26 is dimensioned to pass through the opening 15 in the face shield 12, so that the outer surface 34 of the flange 32 abuts the rescuer's side 22 of the face shield 12 bordering the opening 15 and is sealed thereto (FIG. 12).

The outer end 28 of the cap 26 includes an oval flat outer edge 35 surrounding a protective grading or screen 36. The screen 36 comprises a longitudinal rib 38 intersecting a pair of spaced apart lateral ribs 39.

An oval shaped filter pad 42 having an outer side 44 and an inner side 46 (FIGS. 2 and 17) is supported on the outer edge 35 of the cap 26. The inner side 46 of the pad 42 is opposed to the screen 36 of the cap 26. The filter pad 42 prevents impurities from being transferred through the device 10 from the rescuer to the patient, if such impurities are not sufficiently blocked by the screen 36.

A valve support indicated generally by the reference numeral 48 (FIGS. 6, 7, 8, 13 and 14) supports a valve disc 50 (FIG. 2). The valve support 48 includes an opening 51 extending from the inward end 52 (FIG. 6a) to the outward end 54 of the valve support 48.

Figures 6A, 9, 10:
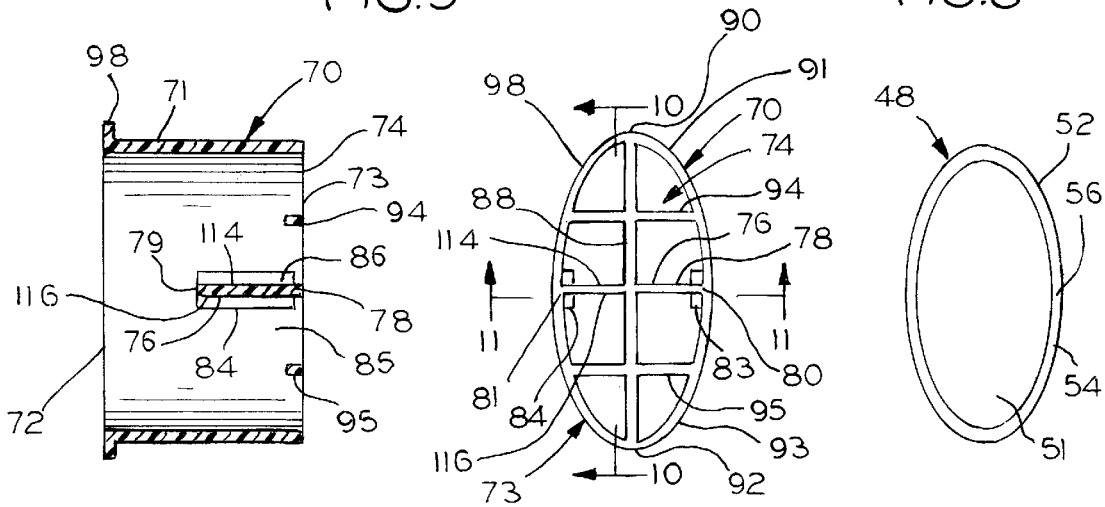
FIG. 6a is a top view of the valve support.
FIG. 9 is a bottom view of the valve support housing (air output end of the device)
FIG. 10 is a longitudinal sectional view of the valve support housing, taken on the plane of the line 10—10 in FIG. 9, and viewed in the direction indicated.

The inward end 52 of the valve support 48 includes an inner, oval edge 56 having a flat surface (FIG. 6a and 7). The filter pad 42 is sandwiched between the inner edge 56 of the valve support 48 and the outer or bottom edge 35 of the cap 26 (FIG. 12), and may be secured to either or both edges 35, 56.

Figure 8:
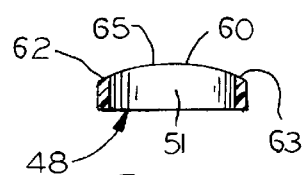
FIG. 8 is a central, lateral, sectional view of the valve seat, taken on the plane of the line 8—8 in FIG. 6, and viewed in the direction indicated.

As may be seen from FIGS. 6, 7 and 8, the outward end 54 of the valve support 48 includes a valve seat 57 having an oval, continuous outer edge 58 forming a concave shape. The oval outer edge 58 comprises a "U" shaped curved segment 59 integrally formed to an inverted "U" shaped curved segment 60, and forming a pair of opposed depressions or troughs 62, 63 at the longitudinal center of the oval outer edge 58. The U shaped segment 59 includes an apex 64; and similarly, the inverted U shaped segment 60 includes an apex 65. The longitudinal length of the outer edge 58 is the distance between apex 64 and apex 65.

The apex 64 and the apex 65 are opposed to each other; and are the outermost points on the valve seat 57. The depressions 62, 63 are positioned substantially midway between the apex 64 and the apex 65 and are laterally opposed to each other. As viewed from FIGS. 6, 7 and 8, the oval edge 58 curves outward (or upward) from the depression 62 to apex 65; curves inward (or downward) from apex 65 to the other depression 63; and curves outward (or downward) to apex 64. Thus, the apex 64 and apex 65 are the outermost points of the valve support 48.

The valve disc 50 (FIG. 2 and 12) has an inner side 66 and an outer side 67. The disc 50 is flexible and pliable and may be formed from a suitable plastic material which is impermeable to air flow. The disc 50 normally when unrestrained has a flat configuration, as shown in FIGS. 2, 18 and 19. The disc 50 Is stressed when Its shape deviates from the normal flat shape. The valve disc 50 is resiliently urged toward the flat shape, when, for example, an external force bending the disc 50 is removed. Hence, the valve disc 50 is stressed when seated on the concave surface 58 of the valve seat 57.

The valve disc 50 is formed to a convex shape or configuration 68 complementary to the concave surface 59 of the valve seat 57, as shown in FIG. 12, When the resuscitator device 10 is in the closed-condition, the convex shape 68 of the valve disc 50 is stressed to cause firm contact with the concave surface 59 of the valve seat 57. The resilient force of the valve disc 50 urges the disc 50 toward an unachievable flat shape due to being blocked by the concave surface 59 of the valve seat 57.

Furthermore, the apexes 64, 65 at the longitudinal ends of the valve seat 57 block the valve disc 50 from resiliently moving from the convex shape to its normal flat configuration such as shown prior to assembly of the parts in FIGS. 2 and 18.

Figure 11:
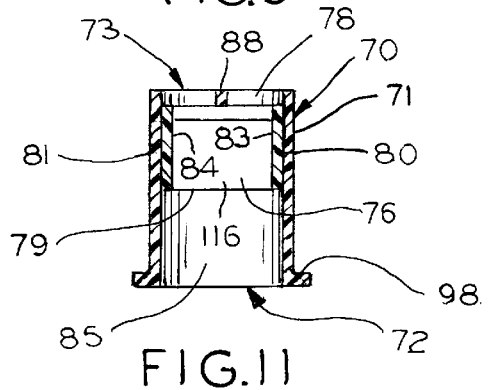
FIG. 11 is a central lateral sectional view of the valve support housing, taken on the plane of the line 11—11 in FIG. 10, and viewed in the direction indicated.

The valve support 48 and the valve disc 50 are secured inside a hollow tubular housing 70 (FIGS. 9, 10 and 11). The housing 70 has an oval or elliptical cross section, taken on the plane of the line perpendicular to the vertical or longitudinal axis of the housing.

The housing 70 comprises an oval inlet end 72 and an oval outlet end 73. The outlet end 73 also includes a protective grading or screen 74 (FIG. 9).

A plate 76 is centrally positioned inside the housing 70 and extends laterally through the longitudinal center of the housing 70. The plate 76 has substantially a square shape and includes an outer edge 78, an inner edge 79; and opposed side edges 80, 81.

A pair of rectangular posts 83, 84 are secured to the inside wall 85 of the housing 70 in an opposed relationship. The side edges 80, 81 of plate 76 are fused or otherwise attached respectively to posts 83 and 84 (FIGS. 11 and 18). Hence, the plate 76 is rigidly positioned inside the housing 70.

As shown in FIG. 9, the screen 74 at the outlet end 73 of the housing 70 includes a longitudinal bar 88 extending centrally along the longitudinal axis of the housing 70, between the vertex 90 of arc 91 and the vertex 92 of the opposite arc 93 of the oval outlet end 73 of the housing 70.

The outer edge 78 of the plate 76 extends laterally at the center of the housing between opposed inside surfaces of the housing at the outlet end 73. Bars 94, 95 are equally spaced from the outer edge 78 of the plate 76 and extend laterally between opposed inside surfaces of the housing 70. The longitudinal bar 88 intersects the lateral bars 94, 95 and the outer edge 78 of the plate 76. Hence, the screen 94 comprises the longitudinal bar 88, lateral bars 94, 95 and the outer edge 78 of the plate 76, to block back flow of foreign matter and contaminants into the device 10 from the patient.

An oval lip 98 extends around the inlet end 72 of the housing 70. The lip 98 is sealed to the patient side 24 of the face shield 12 around the opening 15.

The valve disc 50 has an oval shape having opposed free ends 104, 106 equally spaced from the lateral center portion 108 of the disc 50. Operatively, the valve disc is restrained at the lateral center portion 108 to divide the disc valve 50 into a pair of movable flaps 110, 112.

The lateral center portion 108 of the valve disc 50 is sandwiched between the inner edge 79 of the plate 76 and the surfaces defining the depressions 62, 63 in the valve seat, so that the center portion 108 is in a fixed position.

When forced air is applied to the device 10 at the inner end 18, the flaps 110, 112 bend outward and toward each other to permit air transfer to the victim. Thus, the inner edge 79 of the plate 76 acts as a fulcrum; and flap 110 bends outward and toward side 114 of plate 76 and flap 112 bends outward and toward the opposite side 116 of plate 76.

The outer edge 79 of the plate 76 is attached to the longitudinal bar 88 of the screen 74. The valve disc 50 is dimensioned to be positioned in the housing, so that the lateral center portion 108 on the outer side 66 of disc 50 is opposed to the inner edge 79 of the plate 76 and the lateral center portion 108 on the inner side 67 of disc 50 is opposed to the surfaces defining the depressions 62, 63.

Referring now more specifically to FIGS. 18, 19 and 20, a pair of spaced apart guide rods 122 and 124 are formed on the outer side 66 of the valve disc 50 and extend laterally across the disc at the substantial center thereof, The inner edge 79 of the plate 76 press fits inside the elongated space 125 between the guide rods 122, 124. In this manner, the valve disc 50 is easily positioned inside the resuscitator device 10 at the proper location. Moreover, the attachment of the disc 50 to the plate 76 maintains the lateral center portion 108 of the disc 50 fixedly positioned inside the housing.

Moreover, the guide rods 122, 124 are spaced from the peripheral edges of the valve disc, so that the defining surfaces of the depressions 62, 63 may easily position on the valve disc 50.

When assembling the device 10, the further pad 42 is sealed between the outer end 28 of cap 26 and the inner end 52 of the valve support 48. The assembled cap 26 and valve support 48 are force fitted inside the housing, after the valve disc 50 is positioned in the housing. The lateral center portion 108 of the valve disc rests inside the depressions 62, 63 of the valve support. Therefore, the center portion 108 of the valve disc 50 is restrained by the plate 76 and the valve seat 57, and functions as a hinge.

Prior to using the device 10, the mouth of the victim is cleared of any obstructions. The housing 70 is placed in the mouth of the victim.

The rescuer exhales air under pressure into the resuscitator device 10. The forced air passes through the rescuer or inner end 18 and through the filter pad 42 and into the valve section 17. The valve disc 50 is normally in a closed position. The plate 76 is rigidly secured inside the valve housing 70 to support the valve disc 50 and functions as a hinge for dividing the disc into flaps 110, 112.

Flap 110 pivots or bends outward in a counter clockwise direction away from the input end 25 and toward one side of the plate 76 and the other flap 112 pivots or bends outward in the clockwise direction, away from the input end 18 and toward the other side of plate 76, in response to the forced air applied at the air input end 18 by the rescuer. The forced air rushes past the valve flaps 110, 112 to the patient output end 19 for discharge into the mouth of the patient. After the forced air exhaled by the rescuer has dissipated, the flaps 110, 112 self close to return to their closed-positions.

The surfaces defining the opposed depressions 62, 63 in the valve seat 57 clamp to the peripheral ends of the lateral center portion 108 (FIG. 22). Thus, the plate 76 abuts the outer side of the valve disc 50 and the defining surfaces of the depressions 62, 63 abut the inner side 67 of the valve disc 50. Hence, the peripheral ends of the lateral center portion 18 are sandwiched between the inner edge 79 of the plate 76 and the defining surface of the corresponding depressions 62, 63.

When force fitting the valve support 48 in place, the protruding apexes 59, 60 push the free ends 104, 106 of the valve disc 50 to form the convex shape for the valve disc 50. When The surfaces defining the opposed depressions 62, 63 in the valve seat 57 contact the periphery of the central disc portion 108, the plate 76 prevents any further outward movement of the valve support 48. Hence, the apexes 59, 60 are in their fixed position and cannot move the free ends of the disc 50 any further distance outward.

After the valve support 48 is immovably installed, the apexes 59, 60 block resilient inward movement of the valve disc 50 from resiliently moving inward to form its normal flat shape (FIGS. 2 and 19).

Various modifications of the invention of a resuscitator device described herein, are within the scope of the invention, the scope of which is limited solely and defined by the appended claims

We claim:

1. A device for a rescuer to resuscitate a victim, comprising:

a hollow housing having an input end for inserting forced air into the housing and an output end for discharging said forced air to resuscitate the victim;

a valve seat positioned in said housing between said ends, said valve seat including an opening;

a valve disc having an inner side and an outer side, said disc having an air closed position to close said opening of the seat and an air open position to permit flow of said forced air from the input end to the output end, said valve disc being positioned between the valve seat and the output end of the housing;

plate rigidly secured to the inside of the housing between the output end of the housing and the outer side of the valve disc, said plate have an outer edge and an inner edge, said outer edge of the plate being closer to the outer end of the housing than said inner edge; and a pair of spaced apart rods secured to the outer side of the valve disc, said inner edge of the plate being received between the rods to attach tie disc to the plate for dividing the disc into a pair of movable portions, said portions moving from a closed position to an open position in response to said forced air.

2. The device of claim 1, wherein said rods tend laterally across said valve disc, the inner edge of the plate press fitting in the space between said rods.

3. The device of claim 1, wherein said disc is substantially oval shaped having a lateral width and a longitudinal length, said rods extending laterally across the disc at substantially the longitudinal center thereof.

4. A device for a rescuer to resuscitate a victim, comprising:

a hollow housing having an input end for inserting forced air into the housing and an output end for discharging said forced air to resuscitate the victim;

a valve seat positioned in said housing between said ends, said valve seat including an opening;

a valve disc having an inner side and an outer side, said disc having an air closed position to close said opening of the seat and an air open position to permit flow of said forced air from the input end to the output end, said valve disc being positioned between the valve seat and the output end of the housing;

a plate rigidly secured to the inside of the housing between the output end of the housing and the outer side of the valve disc, said plate having an outer edge and an inner edge, said outer edge of the plate being closer to the outer end of the housing than said inner edge;

attachment means positioned on the outer side of the valve disc, said attachment means securing the disc to the plate to divide the disc into a pair of movable motions, said movable portions moving from a closed position to an open position in response to said forced air;

a first post secured to the inside of the housing;

a second post secured to the inside of the housing in an opposed relationship with said first post; and said plate having a first side edge and a second side edge opposed to the first side edge, said first side edge being attached to said first post and said second side edge being attached to the second post.

5. The device of claim 4, wherein said housing has substantially an oval shape, said plate extending laterally on the inside of the housing from said first side edge to said second side edge.

6. A device for a rescuer to resuscitate a victim, comprising:
- a hollow housing having an input end for inserting forced air into the housing and an output end for discharging said forced air to resuscitate the victim;
- a valve seat positioned in said housing between said ends, said valve seat including an opening;
- a valve disc having an inner side and an outer side, said disc having an air closed position to close said opening of the seat and an air open position to permit flow of said forced air from the input end to the output end, said valve disc being positioned between the valve seat and the output end of the housing;
- a plate rigidly secured to the inside of the housing between the output end of the housing and the outer side of the valve disc, said plate having an outer edge and an inner edge, said outer edge of the plate being closer to the outer end of the housing than said inner edge; and attachment means positioned on the outer side of the valve disc, said attachment means securing the disc to the plate to divide the disc into a pair of movable portions, said movable portions moving from a closed position to an open position in response to said forced air, said valve disc being sandwiched between the inner edge of said plate and said valve seat; and said valve seat being press fitted inside said housing, said valve seat preventing inward movement of the valve disc toward the input end of the housing.

* * * * *